United States Patent
Newton et al.

(10) Patent No.: US 10,309,887 B2
(45) Date of Patent: Jun. 4, 2019

(54) ACOUSTIC IMPACT PARTICLE SIZE MEASUREMENT

(71) Applicant: CiDRA Corporate Services Inc., Wallingford, CT (US)

(72) Inventors: David V. Newton, Madison, CT (US); Mark R. Fernald, Enfield, CT (US)

(73) Assignee: CiDRA Corporate Services Inc., Wallingford, CT (US)

( * ) Notice: Subject to any disclaimer, the term of this patent is extended or adjusted under 35 U.S.C. 154(b) by 338 days.

(21) Appl. No.: 14/762,223

(22) PCT Filed: Jan. 22, 2014

(86) PCT No.: PCT/US2014/012510
§ 371 (c)(1),
(2) Date: Jul. 21, 2015

(87) PCT Pub. No.: WO2014/116675
PCT Pub. Date: Jul. 31, 2014

(65) Prior Publication Data
US 2015/0362418 A1 Dec. 17, 2015

Related U.S. Application Data (60) Provisional application No. 61/755,305, filed on Jan. 22, 2013.

(51) Int. Cl.
*G01N 15/02* (2006.01)
*G01N 29/46* (2006.01)
(Continued)

(52) U.S. Cl.
CPC .......... *G01N 15/02* (2013.01); *G01N 29/046* (2013.01); *G01N 29/09* (2013.01); *G01N 29/14* (2013.01);
(Continued)

(58) Field of Classification Search
CPC ...... G01N 15/02; G01N 29/046; G01N 29/09; G01N 29/14
See application file for complete search history.

(56) References Cited

U.S. PATENT DOCUMENTS 3,218,852 A * 11/1965 Scarpa ............... G01F 1/666
73/861.21
3,477,278 A  11/1969 Lynnworth
(Continued)

OTHER PUBLICATIONS

Ctibor et al. Plasma Spraying and Characterization of Tungsten Carbide-Cobalt Coatings by the Water-Stabilized System WSP. Advances in Materials Science and Engineering. vol. 2009. pp. 1-11. [Retrieved on Apr. 23, 2014]. Retrieved from the Internet: >URL:http://www.hindawi.com/journals/amse/2009/254848/>. entire document.

*Primary Examiner* — Matthew G Marini
(74) *Attorney, Agent, or Firm* — Ware, Fressola, Maguire & Barber LLP (57) ABSTRACT

Apparatus features a signal processor or processing module configured at least to: receive signaling containing information about acoustic emissions resulting from particles impacting a solid sensor element configured in a process pipe having a process fluid flowing therein, including a slurry; and determine particle sizes of solids in the process fluid, based at least partly on the signaling received. The signal processor module may also be configured to provide corresponding signaling containing information about the particle sizes of solids in the process fluid.

34 Claims, 4 Drawing Sheets

Acoustic impact particle size mechanics.

(51) Int. Cl.
  *G01N 29/04* (2006.01)
  *G01N 29/14* (2006.01)
  *G01N 29/22* (2006.01)
  *G01N 29/09* (2006.01)
  *G01N 15/00* (2006.01)

(52) U.S. Cl.
  CPC ........... *G01N 29/222* (2013.01); *G01N 29/46* (2013.01); *G01N 2015/0053* (2013.01); *G01N 2291/02408* (2013.01); *G01N 2291/02416* (2013.01)

(56) References Cited

U.S. PATENT DOCUMENTS

| | | |
|---|---|---|
| 4,674,337 A | 6/1987 | Jonas |
| 5,094,532 A | 3/1992 | Trainer et al. |
| 5,257,530 A | 11/1993 | Beattie et al. |
| 5,333,501 A | 8/1994 | Okada et al. |
| 2006/0058981 A1 | 3/2006 | Volker et al. |
| 2008/0162088 A1* | 7/2008 | DeVaul ................ A61B 5/0024 702/190 |
| 2009/0055104 A1 | 2/2009 | Gysling et al. |

* cited by examiner

Apparatus 10

Signal processor or signal processing module 10a configured at least to receive signaling $S_{in}$ containing information about acoustic emissions resulting from particles impacting a solid sensor element configured in a process fluid structure having a process fluid therein; and determine particle sizes of solids in the process fluid, including a surry, based at least partly on the signaling Sin received; and/or provide corresponding signaling $S_{out}$ containing information about the particle sizes of solids in the process fluid.

One or more other module/components 10b, including input/output components/modules, memory (RAM, ROM, EPROM, etc.), data, control and address busing architecture, etc.

Figure 1.

Figure 2. Acoustic impact particle size mechanics.

Fig.3a                          Fig. 3b

Figure 3. Acoustic impact signal processing

Figure 4. Shape changes caused by different particle size distributions

Figure 5. Experimental Data

ACOUSTIC IMPACT PARTICLE SIZE MEASUREMENT

CROSS-REFERENCE TO RELATED APPLICATIONS

This application corresponds to international patent application Ser. No. PTC/US2014/012510, filed 22 Jan. 2014, which claims benefit to provisional patent application ser. no. 61/755,305 (CCS-0120), filed 22 Jan. 2013, which is incorporated by reference in their entirety.

BACKGROUND OF THE INVENTION

1. Field of Invention

The present invention relates to a technique for measuring a particle size in process fluid; and more particular to a technique for measuring a particle size in process fluid, such a slurry, using an acoustic impact based approach.

2. Description of Related Art

When processing certain types of process fluid, including a slurry, there is a need for measuring the size of particles flowing in such a process fluid. In one particular example, e.g., in the mining industry, rubber lined pipes are used for slurry transport. Rubber is typically used because it provides an effective method of preventing pipe wear. However, the rubber hinders detection of high frequency acoustic energy (caused by particle impacts) from outside of the pipe.

There is a need for a solution to this problem in the art.

SUMMARY OF THE INVENTION

In summary, the present invention provides a new and unique technique, including a new method and apparatus, of measuring a particle size distribution of solids in a process flow, e.g., including a slurry, that uses the acoustic emission resulting from particles impacting a solid sensor element. The technique involves inserting a solid sensor element having an impact body into the flow of slurry. Particles in the slurry are able to impact the body. Particle impacts generate acoustic impulses in the body, and the body acts as a waveguide that transmits acoustic impulse energy to an ultrasonic transducer. The frequency content of the acoustic impulse energy is understood to be a function of the particle size distribution. Particularly, the shape and amplitude of an acoustic signal power spectral density at ultrasonic frequencies (>20 kHz) are understood to depend on the distribution of the particles in the slurry. Low frequency acoustic energy (<10 kHz), which is dependent on environmental noise and not particle size, may be isolated from the ultrasonic transducer by mechanical and electronic filtering.

The uniqueness of the present invention comes from a mechanics and signal processing technique used to capture and convert acoustic impulse signals to a particle size distribution. According to a known Hertz theory of impact between solid bodies, the contact time of the bodies and impulse amplitude is dependent on the diameter of the bodies. After converting from a time domain to a frequency domain, the Hertz impact theory indicates that the frequency content and amplitude of the acoustic impact signal will change based on the particle diameter. In more general terms, the shape of a power spectral density spectrum is understood to be dependent on the size distribution of the impacting particles.

Examples of Particular Embodiments

In particular, and according to some embodiments, the present invention may include, or take the form of, apparatus featuring a signal processor or processing module configured at least to:
 receive signaling containing information about acoustic emissions resulting from particles impacting a solid sensor element configured in a process pipe having a process fluid flowing therein, including a slurry; and
 determine particle sizes of solids in the process fluid, based at least partly on the signaling received.

According to some embodiment of the present invention, the signal processor module may be configured to provide corresponding signaling containing information about the particle sizes of solids in the process fluid.

The present invention may also include one or more of the following features:

The signal processor or signal processing module may be configured to determine a particle size distribution of the solids in the process fluid, based at least partly on the signaling received.

The signaling may contain information about particle impacts that generate acoustic impulses in the solid sensor element, which acts like a waveguide that transmits acoustic impulse energy to a transducer, including an ultrasonic transducer, in the solid sensor element.

The apparatus may include the solid sensor element configured with an impact body and a transducer, e. g., including an ultrasonic transducer, so that particle impacts generate acoustic impulses in the impact body, which acts like a waveguide that transmits acoustic impulse energy to the transducer.

The frequency content of the acoustic impulse energy may be understood to be a function of a particle size distribution.

The shape and amplitude of an acoustic signal power spectral density at ultrasonic frequencies, e. g., greater than 20 kHz, may be understood to depend on a distribution of the particles in the process fluid.

Low frequency acoustic energy, e.g., less than 10 kHz, which is dependent on environmental noise and not particle size, may be isolated from an ultrasonic transducer by mechanical and electronic filtering.

The signaling may be acoustic impulse signaling; and the signal processor or signal processing module may be configured to convert the acoustic impulse signaling to a particle size distribution using a signal processing algorithm based at least partly on the Hertz theory of impact between solid bodies, including where contact time of the solid bodies and impulse amplitude is dependent on the diameter of the solid bodies.

The signal processor or signal processing module may be configured to make the determination by converting from a time domain to a frequency domain, where the Hertz theory indicates that a frequency content and amplitude of an acoustic impact signal will change based on a particle diameter.

The signal processor or signal processing module may be configured to determine a particle size distribution of impacting particles, based at least partly on the shape of a power spectral density spectrum being dependent on a size distribution of impacting particles.

The solid sensor element may be configured with an ultra-hard, high wear coating in order to withstand the process fluid, including a tungsten carbide plasma coating.

The acoustic impedance of the solid sensor element may be configured to substantially match a base material of the impact body so that the solid sensor element does not act as a barrier to acoustic signaling.

The solid sensor element may be configured in a double threaded sleeve.

The double threaded sleeve may be made from a material that has different acoustic impedance than the solid sensor element.

The double threaded sleeve may be configured with a threaded interface having an angle that acts to disperse unwanted acoustic noise.

The signaling may contain information about the acoustic emissions in a series of snapshots, each snapshot having a predetermined time duration, and each snapshot in time containing information about acoustic energy generated by impacts from particles of all sizes in the process fluid.

The signal processor or signal processing module may be configured to calculate for each waveform collected and received a spectral density, e.g., using a Discrete Fast Fourier Transform (DFFT).

The signal processor or signal processing module may be configured to smooth a frequency spectrum for each waveform, e.g., using a ⅓ octave filter.

The signal processor or signal processing module may be configured to average the series of snapshots in order to smooth out variations caused by outliers.

The signal processor or signal processing module may be configured to interpret the ⅓ octave power spectrum in order to determine a particle size distribution.

The signal processor or signal processing module may be configured to determine the particle size distribution, e.g., based at least partly on some combination of a change in either:

the slope of an acoustic impact signal, or the amplitude in particular frequency bins which changes with a mean particle size.

By way of example, the signal processor or signal processing module may be configured with at least one processor and at least one memory including computer program code, and the at least one memory and computer program code may be configured, with the at least one processor, to cause the apparatus at least to receive the signaling and determine the particle sizes of solids in the process fluid, based at least partly on the signaling received.

The Method

According to some embodiments, the present invention may also include, or take the form of, a method or process that includes steps for receiving in a signal processor or signal processing module signaling containing information about acoustic emissions resulting from particles impacting a solid sensor element configured in a process pipe having a process fluid flowing therein, including a slurry; and determining in the signal processor or signal processing module the particle sizes of solids in the process fluid, based at least partly on the signaling received.

The method may include providing with the signal processor or signal processing module corresponding signaling containing information about the particle sizes of solids in the process fluid, as well as one or more of the features set forth herein, according to some embodiments of the present invention.

BRIEF DESCRIPTION OF THE DRAWING

The drawing includes FIGS. 1-5, which are not necessarily drawn to scale, as follows.

DETAILED DESCRIPTION OF BEST MODE OF THE INVENTION

Figure 1:
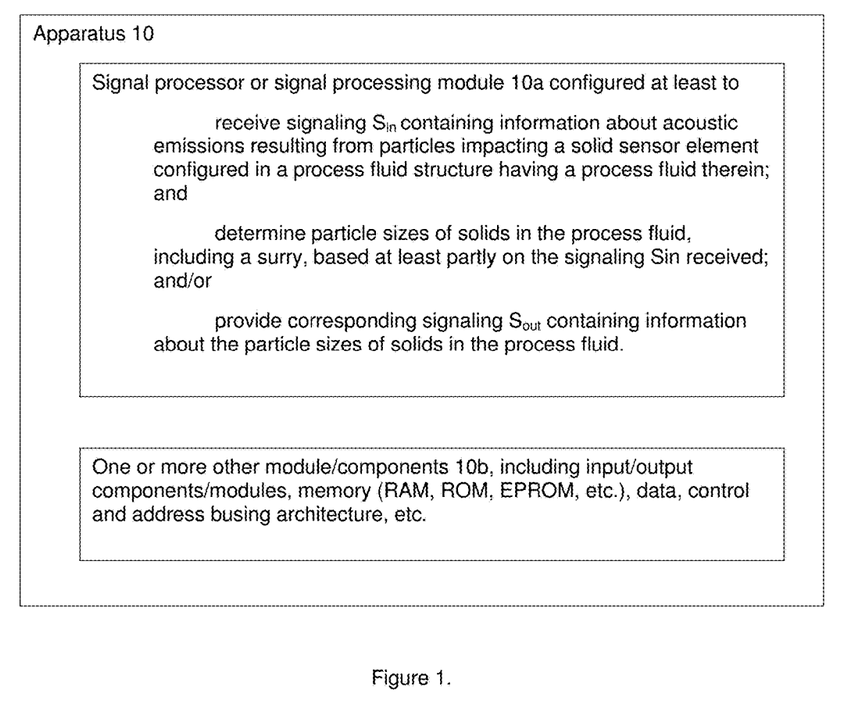
FIG. 1 is a block diagram of apparatus having a signal processor or signal processing module, according to some embodiments of the present invention.

FIG. 1 : The Basic Apparatus 10

Figure 2:
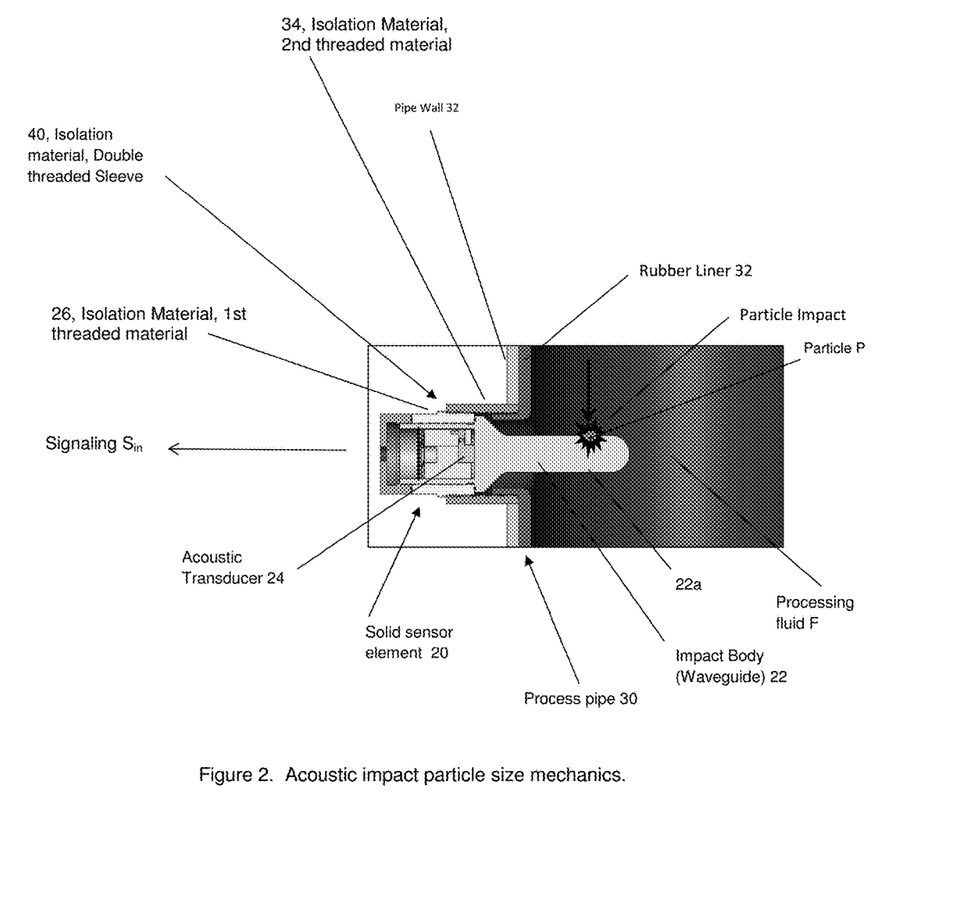
FIG. 2 shows a diagram of one example for implementing an acoustic impact particle size mechanics, according to some embodiments of the present invention FIG. 3 includes FIGS. 3a and 3b, where

FIG. 1 shows one embodiment of the present invention in the form of apparatus 10 configured with a signal processor or processing module 10a for implementing the basic signal processing functionality according to some embodiments of the present invention. The signal processor or processing module 10a may be configured at least to:

receive signaling $S_{in}$ containing information about acoustic emissions resulting from particles P impacting a solid sensor element 20 configured in a process pipe 30 having a process fluid F flowing therein, including a slurry, consistent with that shown in FIG. 2; and determine particle sizes of solids in the process fluid F, based at least partly on the signaling $S_{in}$ received.

The signal processor or processing module 10a may also be configured to provide corresponding signaling $S_{out}$ containing corresponding information about the particle sizes of solids in the process fluid F, e.g., including in the form of control signaling that may be provided and used to modify the processing of the process fluid F in the process pipe 30.

The scope of the invention is not intended to be limited to the type or kind of use of the corresponding signaling $S_{out}$ containing information about the particle sizes of solids in the process fluid F, including for further processing, printing or displaying, as well as for other types or kinds of uses either now known or later developed in the future.

Further, the scope of the invention is not intended to be limited to the type or kind of process fluid F contained, processed or flowing in the process pipe 30, as well as a tank, a cell or a vessel, etc. For example, the scope of the invention is intended to include processing fluids that are either now known or later developed in the future. Moreover, the scope of the invention is not intended to be limited to the type or kind of industrial process of which the process fluid F is being processed, including a process or processes that is or are either now known or later developed in the future.

The apparatus 10 may also include other circuits, components or modules 10b to implement the functionality of the signal processor or processing module 10a either now known or later developed in the future, e.g., including memory modules, input/output modules, data and busing architecture and other signal processing circuits, wiring or components, consistent with that known by a person skilled in the art, and/or consistent with that set forth herein.

FIG. 2

By way of example, FIG. 2 shows an example of acoustic impact particle size mechanics for implementing one embodiment of a mechanical setup that may be used to generate acoustic impact signals. In FIG. 2, the solid sensor element 20 may be configured in relation to the process pipe generally indicated as 30. The solid sensor element 20 may include an impact body 22, an acoustic transducer 24, and an isolation material 26. The process pipe 30 has the process fluid F flowing therein, that may take the form of a slurry having particles P flowing therein. The process pipe 30 may include a pipe wall 32, a rubber liner 32 and corresponding isolation material 34, as shown By way of example, in the mining industry rubber lined pipes like process pipe 30 are typically used for slurry transport. Rubber is typically used because it provides an effective method of preventing pipe wear. However, the rubber hinders detection of high frequency acoustic energy (caused by particle impacts) from outside of the pipe. One aspect of the present invention is the use of the solid sensor element 20 having the impact body 22 in the slurry flow in order to bypass the rubber liner 32. The particles P in the slurry S impact the body 22, and the body 22 acts as a waveguide to conduct the acoustic impulse signal to the acoustic transducer 24, e.g., an ultrasonic transducer. According to some embodiments, the impact body 22 may be coated with an ultra-hard, high wear coating 22a in order to withstand the slurry flow, which can be corrosive and abrasive. In this case, and by way of example, a tungsten carbide plasma coating may be used. The coating 22a should be harder than the particles P in the slurry in order to withstand corrosion/erosion. Additionally, the acoustic impedance of the coating layer 22a should substantially match the base material of the body 22 so that the coating 22a does not act as a barrier to the acoustic signal. In order to decouple any acoustic energy that is not related to the particle size distribution, an isolation material may be introduced.

In one embodiment, e.g., a double threaded sleeve 40 may be configured using a combination of a 1st threaded isolation material 26 and a 2nd threaded isolation material 34. The double threaded sleeve 40 may be made from a material that has a different acoustic impedance than the impact body 22. The impedance mismatch between the two may be configured to cause external acoustic noise (acoustic energy not related to particle size) to be reflected away from the probe or solid sensor element 20. Additionally, the angle of the threaded interface may be configured to act to disperse unwanted acoustic noise.

The Signal Processing Technique

Figures 3A, 3B:
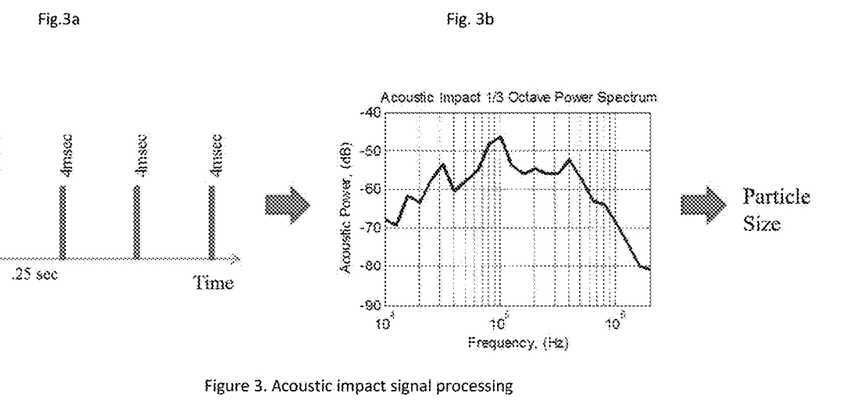
FIG. 3a shows a time line having acoustic signals arriving in 4 millisecond intervals, and where
FIG. 3b shows a graph of acoustic power (dB) versus frequency (Hz) having a plot of an acoustic impact ⅓ octave power spectrum, from which particle size may be determined.

FIG. 3 shows schematically at least in part an example of an acoustic impact signal processing technique that may be used to convert the acoustic impulse energy to the particle size distribution, which is described in further detail below. The acoustic signal may be captured, e.g., using a high frequency digitizer. In order to resolve high frequency acoustic impacts, the acoustic signals may be, e.g., sampled above 5 MHz. By way of example, the signal processing sequence may be implemented, e.g., by the signal processor or signal processing module 10a, as follows:

1. A 4 millisecond waveform may be collected. This 4 millisecond waveform is essentially a snapshot in time of the acoustic energy generated by impacts from particles P of all sizes in the slurry S (FIG. 2). The 4 millisecond duration can be longer or shorter depending on the frequency resolution required.

2. For each 4 millisecond waveform collected, the power spectral density may be calculated and determined, e.g., using a Discrete Fast Fourier Transform (DFFT).

3. The frequency spectrum may then be smoothed, e.g., using a ⅓ octave filter. The ⅓ octave filtering may be used because the energy in the octave bands is substantially constant. However, other types or kinds of smoothing techniques such a fixed window can also be used, that are either now known or later developed in the future.

4. The steps above may be repeated, e.g., every 0.25 seconds or faster. The results may then be averaged in order to smooth out variations caused by outliers.

Figure 4:
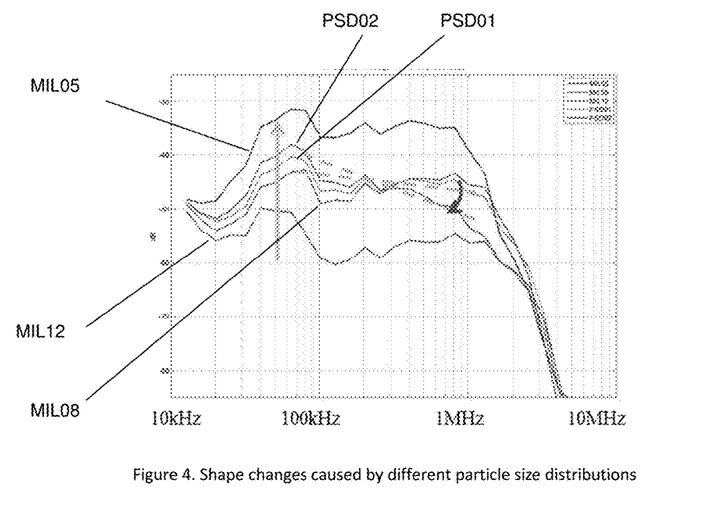
FIG. 4 shows a graph of acoustic power (dB) versus frequency (MHz) having five (5) plots of acoustic impact ⅓ octave power spectrums having designations MIL05, MIL08, MIL12, PSD01 and PSD02, indicating shape changes caused by different particle size distributions.
Figure 5:
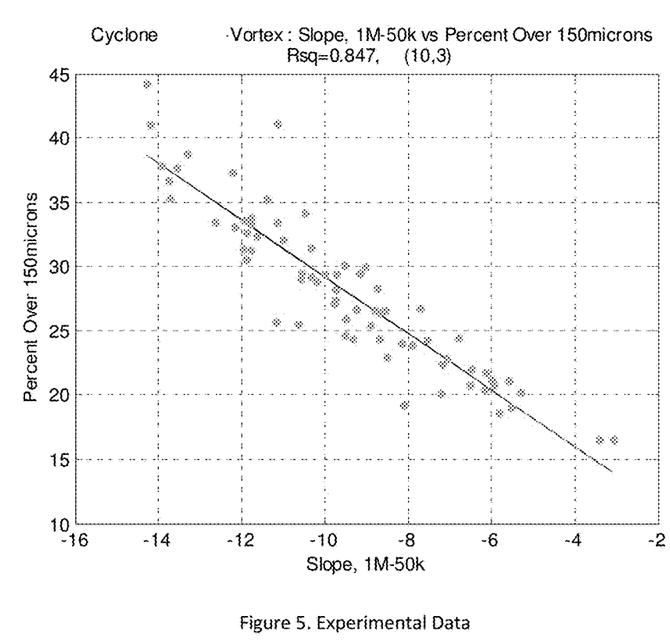
FIG. 5 shows a graph of percentage over 150 microns versus slope, 1 M-50 k showing experimental data.

5. The ⅓ Octave Power Spectrum may then be interpreted to determine the particle size distribution. For instance, the slope from 100 kHz to 1 MHz will change as the particle size distribution changes. Additionally, the amplitude in particular frequency bins changes with mean particle size. consistent with that shown in FIG. 4, the combination of these changes may be used to determine a feature of the particle size distribution that is of interest. As an example, in order to measure the % of particles over 100 mesh (150 microns), the 50 kHz-1 Mhz difference can be used. FIG. 5 shows some experimental data showing the correlation between the particle size+100 mesh and the slope of the acoustic impact signal.

Signal Processor or Signal Processing Module 10a

By way of example, and consistent with that described herein, the functionality of the signal processor or processing module 10a may be implemented to receive the signaling $S_{in}$, process the signaling $S_{in}$, and/or provide the corresponding signaling $S_{out}$, using hardware, software, firmware, or a combination thereof, although the scope of the invention is not intended to be limited to any particular embodiment thereof. In a typical software implementation, the signal processor or processing module 10a may include, or take the form of, one or more microprocessor-based architectures having a microprocessor, a random access memory (RAM), a read only memory (ROM), input/output devices and control, data and address busing architecture connecting the same. A person skilled in the art would be able to program such a microprocessor-based implementation to perform the functionality set forth herein, as well as other functionality described herein without undue experimentation. The scope of the invention is not intended to be limited to any particular implementation using technology either now known or later developed in the future. Moreover, the scope of the invention is intended to include a signal processor, device or module 10a as either part of the aforementioned apparatus, as a stand alone module, or in the combination with other circuitry for implementing another module.

Techniques for receiving signaling in such a signal processor or processing module 10a are known in the art, and the scope of the invention is not intended to be limited to any particular type or kind thereof either now known or later developed in the future. Based on this understanding, a person skilled in the art would appreciate, understand and be able to implement and/or adapt the signal processor or processing module 10a without undue experimentation so as to receive signaling $S_{in}$ containing information about acoustic emissions resulting from particles impacting a solid sensor element like element 20 configured in a process pipe like element 30 having a process fluid like element F flowing therein, including a slurry, and determine particle sizes of solids in the process fluid F, based at least partly on the signaling $S_{in}$ received, consistent with that set forth herein.

It is also understood that the apparatus 10 may include one or more other modules, components, processing circuits, or circuitry 10b for implementing other functionality associated with the underlying apparatus that does not form part of the underlying invention, and thus is not described in detail herein. By way of example, the one or more other modules, components, processing circuits, or circuitry may include random access memory, read only memory, input/output circuitry and data and address buses for use in relation to implementing the signal processing functionality of the signal processor, or devices or components, etc.

Applications

By way of example, the present invention may be used in, or form part of, or used in conjunction with, industrial processes like a mineral extraction processing system for extracting or separating minerals in a fluidic medium that are either now known or later developed in the future, including any mineral process, such as those related to processing substances or compounds that result from inorganic processes of nature and/or that are mined from the ground, as well as including either other extraction processing systems or other industrial processes, where the extraction, or separating, or sorting, or classification, of product by size, or density, or some electrical characteristic, is critical to overall industrial process performance.

The Scope of the Invention

While the invention has been described with reference to an exemplary embodiment, it will be understood by those skilled in the art that various changes may be made and equivalents may be substituted for elements thereof without departing from the scope of the invention. In addition, may modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention.

What is claimed is:

1. Apparatus comprising:
   a solid sensor element configured in a process pipe having a process fluid flowing therein, the solid sensor element having an impact body configured to extend into the process pipe, the solid sensor element being configured to a pipe wall in a double threaded sleeve that is made from a material that has a different acoustic impedance than the impact body, the double threaded sleeve having a combination of a first threaded isolation material and a second threaded isolation material, the first threaded isolation material being threaded to the solid sensor element, the second threaded isolation material having two sides, each side having respective threads, a first side of the second threaded isolation material being threaded to the first threaded isolation material, and a second side of the second threaded isolation material being threaded to a rubber liner of the process pipe; and a signal processor or signal processing module configured at least to:
   receive signaling containing information about acoustic emissions resulting from particles impacting the solid sensor element configured in the process pipe having the process fluid flowing therein, including a slurry; and
   determine corresponding signaling containing information about particle sizes of solids in the process fluid, based at least partly on the signaling received.

2. Apparatus according to claim 1, wherein the signal processor or signal processing module is configured to provide the corresponding signaling containing information about the particle sizes of solids in the process fluid.

3. Apparatus according to claim 1, wherein the signal processor or signal processing module is configured to determine a particle size distribution of the solids in the process fluid, based at least partly on the signaling received.

4. Apparatus according to claim 1, wherein the signaling contains information about particle impacts that generate acoustic impulses in the solid sensor element, which acts like a waveguide that transmits acoustic impulse energy to a transducer, including an ultrasonic transducer, in the solid sensor element.

5. Apparatus according to claim 1, wherein the apparatus comprises the solid sensor element configured with the impact body and a transducer, including an ultrasonic transducer, so that particle impacts generate acoustic impulses in the impact body, which acts like a waveguide that transmits acoustic impulse energy to the transducer.

6. Apparatus according to claim 5, wherein the frequency content of the acoustic impulse energy is a function of a particle size distribution.

7. Apparatus according to claim 5, wherein the shape and amplitude of an acoustic signal power spectral density at ultrasonic frequencies greater than 20 kHz will depend on a distribution of the particles in the process fluid.

8. Apparatus according to claim 7, wherein low frequency acoustic energy less than 10 kHz, which is dependent on environmental noise and not particle size, is isolated from an ultrasonic transducer by mechanical and electronic filtering.

9. Apparatus according to claim 1, wherein
   the signaling is acoustic impulse signaling; and
   the signal processor or signal processing module is configured to convert the acoustic impulse signaling to a particle size distribution using a signal processing algorithm based at least partly on the Hertz theory of impact between solid bodies, including where contact time of the solid bodies and impulse amplitude is dependent on the diameter of the solid bodies.

10. Apparatus according to claim 9, wherein the signal processor or signal processing module is configured to make the determination by converting from a time domain to a frequency domain, where the Hertz theory indicates that a frequency content and amplitude of an acoustic impact signal will change based on a particle diameter.

11. Apparatus according to claim 9, wherein the signal processor or signal processing module is configured to determine a particle size distribution of impacting particles, based at least partly on the shape of a power spectral density spectrum being dependent on a size distribution of impacting particles.

12. Apparatus according to claim 1, wherein the solid sensor element is configured with an ultra-hard, high wear coating in order to withstand the process fluid, including a tungsten carbide plasma coating.

13. Apparatus according to claim 1, wherein the acoustic impedance of the solid sensor element substantially matches a base material of the impact body so that the solid sensor element does not act as a barrier to acoustic signaling.

14. Apparatus according to claim 1, wherein the double threaded sleeve is configured with a threaded interface having an angle that acts to disperse unwanted acoustic noise.

15. Apparatus according to claim 1, wherein the signaling contains information about the acoustic emissions in a series of snapshots, each having a predetermined time duration, and each snapshot in time containing information about acoustic energy generated by impacts from particles of all sizes in the process fluid.

16. Apparatus according to claim 15, wherein the signal processor or signal processing module is configured to calculate for each waveform collected and received a spectral density using a Discrete Fast Fourier Transform (DFFT).

17. Apparatus according to claim 16, wherein the signal processor or signal processing module is configured to smooth a frequency spectrum for each waveform using a ⅓ octave filter.

18. Apparatus according to claim 17, wherein the signal processor or signal processing module is configured to average the series of snapshots in order to smooth out variations caused by outliers.

19. Apparatus according to claim 17, wherein the signal processor or signal processing module is configured to interpret the ⅓ octave power spectrum in order to determine a particle size distribution.

20. Apparatus according to claim 19, wherein the signal processor or signal processing module is configured to determine the particle size distribution, based at least partly on some combination of a change in either:
the slope of an acoustic impact signal, or
the amplitude in particular frequency bins which changes with a mean particle size.

21. Apparatus according to claim 1, wherein the signal processor or signal processing module is configured with at least one processor and at least one memory including computer program code, and the at least one memory and computer program code is configured, with the at least one processor, to cause the apparatus at least to receive the signaling and determine the corresponding signaling containing information about the particle sizes of the solids in the process fluid, based at least partly on the signaling received.

22. Apparatus according to claim 1, wherein the process pipe includes a pipe wall and a rubber liner.

23. Apparatus according to claim 22, wherein the second threaded isolation material is threaded to the rubber liner using a threaded arrangement.

24. Apparatus according to claim 23, wherein the second threaded isolation material includes threads, the rubber liner includes corresponding threads, and the threaded arrangement includes the threads and corresponding threads coupled together.

25. Apparatus according to claim 1, wherein the first threaded isolation material has two sides, each side having respective threads, and a first side of the first threaded isolation material being threaded to the solid sensor element, and a second side of the first threaded isolation material being threaded to the second threaded isolation material.

26. Apparatus according to claim 1, wherein the apparatus is an acoustic impact particle measurement device.

27. A method comprising:
configuring a solid sensor element in a process pipe having a process fluid flowing therein, the solid sensor element having an impact body configured to extend into the process pipe, the solid sensor element being configured to a pipe wall in a double threaded sleeve that is made from a material that has a different acoustic impedance than the impact body, the double threaded sleeve having a combination of a first threaded isolation material and a second threaded isolation material, the first threaded isolation material being threaded to the solid sensor element, the second threaded isolation material having two sides, each side having respective threads, a first side of the second threaded isolation material being threaded to the first threaded isolation material, and a second side of the second threaded isolation material being threaded to a rubber liner of the process pipe; and
receiving in a signal processor or signal processing module signaling containing information about acoustic emissions resulting from particles impacting the solid sensor element configured in the process pipe having the process fluid flowing therein, including a slurry; and
determining in the signal processor or signal processing module corresponding signaling containing information about particle sizes of solids in the process fluid, based at least partly on the signaling received.

28. A method according to claim 27, wherein the method comprises providing with the signal processor or signal processing module the corresponding signaling containing information about the particle sizes of solids in the process fluid.

29. A method according to claim 27, wherein the method comprises determining in the signal processor or signal processing module a particle size distribution of the solids in the process fluid, based at least partly on the signaling received.

30. A method according to claim 27, wherein the signaling contains information about particle impacts that generate acoustic impulses in the solid sensor element, which acts like a waveguide that transmits acoustic impulse energy to a transducer, including an ultrasonic transducer, in the solid sensor element.

31. A method according to claim 27, wherein the method comprises configuring the solid sensor element with the impact body and a transducer, including an ultrasonic transducer, so that particle impacts generate acoustic impulses in the impact body, which acts like a waveguide that transmits acoustic impulse energy to the transducer.

32. Apparatus comprising:
means for configuring a solid sensor element in a process pipe having a process fluid flowing therein, the solid sensor element having an impact body configured to extend into the process pipe, the means for configuring comprising a double threaded sleeve that is made from a material that has a different acoustic impedance than the impact body, the double threaded sleeve having a combination of a first threaded isolation material and a second threaded isolation material, the first threaded isolation material being threaded to the solid sensor element, the second threaded isolation material having two sides, each side having respective threads, a first side of the second threaded isolation material being threaded to the first threaded isolation material, and a second side of the second threaded isolation material being threaded to a rubber liner of the process pipe; and means for receiving signaling containing information about acoustic emissions resulting from particles impacting the solid sensor element configured in a process pipe having a process fluid flowing therein, including a slurry; and means for determining corresponding signaling containing information about particle sizes of solids in the process fluid, based at least partly on the signaling received.

33. Apparatus according to claim 32, wherein the apparatus further comprises means for providing the corresponding signaling containing information about the particle sizes of solids in the process fluid.

34. Apparatus according to claim 32, wherein the means for determining particle sizes of solids in the process fluid includes determining a particle size distribution of the solids in the process fluid.

\* \* \* \* \*